US00PP10605P

United States Patent [19]

Egger

[11] Patent Number: Plant 10,605

[45] Date of Patent: Sep. 15, 1998

[54] LONGIFLORUM×ASIATIC HYBRID LILY PLANT NAMED 'CEB QUEST'

[75] Inventor: Donald L. Egger, Wilsonville, Oreg.

[73] Assignee: Cebeco Lilies, Inc., Aurora, Oreg.

[21] Appl. No.: 691,041

[22] Filed: Aug. 7, 1996

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Klarquist Sparkman Campbell Leigh & Whinston, LLP

[57] ABSTRACT

A new and distinct Lily hybrid having upright, large, soft purple pink colored flowers with a distinctive pattern of spotting on tall, strong stems excellent for cut flower production.

1 Drawing Sheet

BACKGROUND OF THE INVENTION

The present invention relates to a new and distinct cultivar of Lily hybrid referred to commercially as a Longiflorum-Asiatic Lily Hybrid and named 'CEB Quest'. This invention was developed by controlled breeding using an unselected Ace × P.W. seedling as the seed parent and PAM #2 as the pollen parent.

The Longiflorum-Asiatic cross is relatively new to the trade. This type of cross was originally made to create colored *Lilium longiflorum* hybrids. Instead, due to the difficulty in crossing back to *L. longiflorum*, the plants that were developed have been crossed with Asiatic lilies. As such, the results look more like Asiatic lilies. The resulting hybrids have several advantages over an Asiatic lily: (1) often larger flowers; (2) often larger, waxier leaves; (3) hybrid vigor; (4) lower susceptibility to leaf scorch; (5) excellent flower texture and substance; (6) often more virus resistance; (7) new and clearer colors; and (8) stronger, sturdier stems.

This invention has not been observed under all possible environmental conditions. The phenotype may vary significantly with variations in environment such as temperature, light intensity, and day length, without, however, any variation in genotype.

The following traits have been repeatedly observed and are determined to be the basic characteristics of this invention which in combination distinguish this lily as a new and distinct cultivar: (1) large, upright flowers of a light purple pink color with a distinctive prominent pattern of spotting and a light orange blush which fades to white; (2) very early bloom; (3) good bud color; (4) tall, uniform strong stems; (5) excellent vase life; and (6) excellent field bulb production characteristics. Bulbs of this plant may be precooled and forced out of season for very uniform cut flower production.

To the breeder's knowledge, there are no other Longiflorum-Asiatic lily hybrids with this color flower suitable for cut flower forcing on the market.

Asexual reproduction of this new variety has been accomplished at Cebeco Lilies, Inc., in Aurora, Oreg. by scaling. The resulting plants have shown that the above-mentioned unique features are stable and reproduce true to type in each successive propagation.

Figure 1:
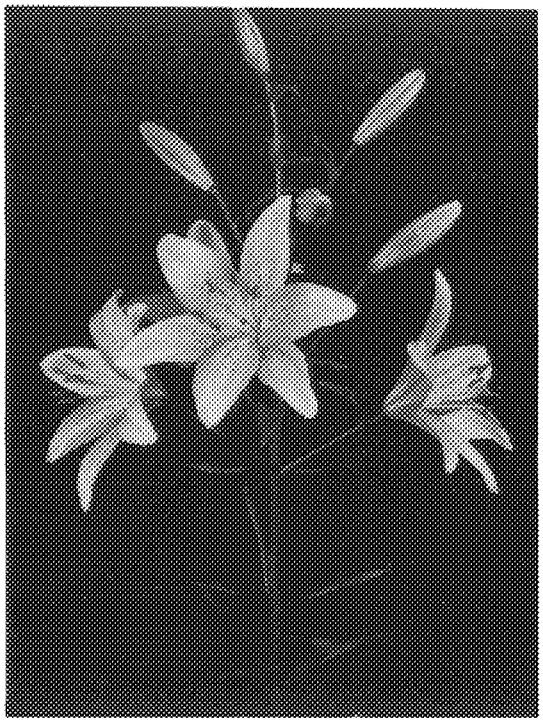
FIG. 1 is a photograph showing the 'CEB Quest' lily.
Figure 2:
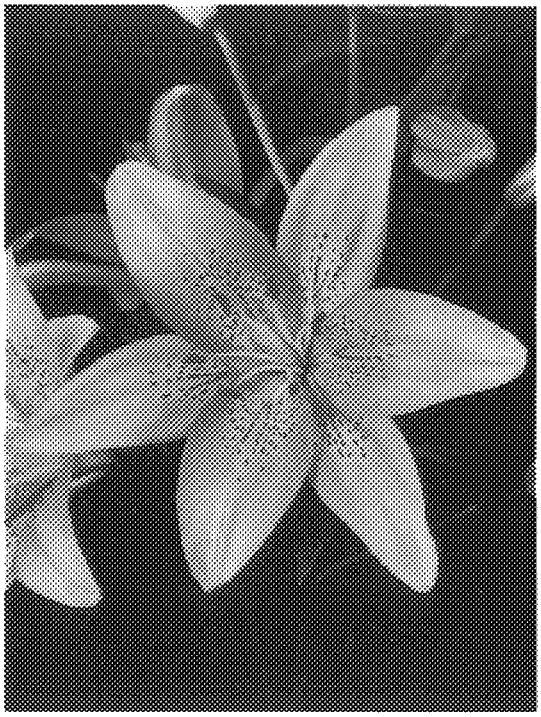
FIG. 2 is a close-up photograph which illustrates in greater detail a single flower of the new plant.

The photographs of the drawing were taken in August 1993 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. greenhouses in Aurora, Oreg. in July 1993. Color references are made to The Royal Horticultural Society Colour Chart, except where the context indicates a term having its ordinary dictionary meaning.

The Plant

Origin: Seedling.

Parentage:

*Seed parent.*—An unselected Ace × P.W. seedling.

*Pollen parent.*—Pam #2.

Commercial classification: Upright longiflorum-Asiatic hybrid, cut flower type.

Classification: Division VIII, according to the Horticultural Classification of Lilies by The Royal Horticultural Society of London.

Form: Single erect stem bearing terminal cluster of flowers.

Height: About 80 cm. from the top of the soil to the top of the flowers from bulbs of 12 cm. in circumference.

Growth habit: Vigorous, upright and rigid.

Internode length: About 5–15 mm.

Foliage:

*Arrangement.*—Spiral.

*Quantity.*—Average.

*Leaf size.*—Variable. To about 13.5 cm. long and about 8 mm. wide.

*Leaf shape.*—Lanceolate with entire margins.

*Texture.*—Leathery.

*Aspect.*—Glossy.

*Color.*—Medium green on both sides, 147A.

Bulbs:

*Size.*—Variable, ranging to about 12–14 cm. in circumference as used commercially.

*Color.*—White.

The Bud

Size: Very large, to about 10.5 cm. long and 3 cm. wide just prior to opening.

Shape: Ovoid with an obtuse tip.

Rate of opening: The mature bud opens slowly in response to light.

Color: Purple pink with lime green streaks at seams and tip (Grayed-Purple Group 186B with Yellow Green Group 144A-B).

The Flower

Blooming habit: Annually, once and early season.

Days to bloom: Flowers approximately 67 days after spring greenhouse planting under typical commercial flower forcing conditions of 15 degrees Celsius night time temperatures.

Inflorescence size: About 28 cm. high and 28 cm. wide when there are six flowers present.

Flower size: Large.

*Diameter.*—About 18 cm.

*Depth.*—About 7 cm.

Borne: In an umbel or modified raceme of 5 to 10 flowers from bulbs 12–14 cm. in circumference.

Shape: When the flower first opens it is bowl shaped. Later, the shape flattens out and the tepals reflex slightly at the tips.

Tepalage:

*Number.*—Six.

*Arrangement.*—Imbricated.

*Shape.*—Ovate.

*Texture.*—Leathery, thick.

*Aspect.*—Satiny.

*Size.*—Length: About 11 cm. Width: Inner tepals—about 50 mm. Outer tepals—about 38 mm.

*Depth of Imbrication.*—About 2 cm.

Nectary: About 3 cm. long; purple pink; pubescent; with the channels close together.

Projections: Few, terminating with spots.

Spots: Long, oval spots in a distinctive, prominent pattern of linear trails on the bottom half of the tepals.

Blush: Creamy white, Yellow-White Group 158B fading to white, Yellow-White Group 158D.

Color:

*Topside.*—Soft purple pink, Grayed Purple Group 186A-C.

*Bottomside.*—Purple pink, Grayed-Purple Group 186A-B.

Discoloration: When the blush fades, the whole tepal is a clearer purple pink.

Fragrance: Slight.

Lasting quality: Excellent.

Pedicle:

*Length.*—Usually about 4–12 cm.

*Color.*—Yellow green (144A).

*Orientation.*—Ascending upwardly from about 45° from the horizontal.

The Reproductive Organs

Stamens:

*Number.*—Six, typical of the genus Lilium.

*Anthers before dehiscence.*—Size: About 2.5 cm. Color: Grayed-Orange Group 172C.

*Filaments.*—Length: About 7 cm. Color: Dull pink. Grayed-Purple Group 186D at the top to white at the base.

*Pollen.*—Color: Orange. Grayed-Orange Group 169B.

Pistil:

*Number.*—One.

*Style.*—Length: About 5 cm. Color: Grayed-Orange Group 173C near stigma to Grayed-Red Group 181C to creamy white at base.

*Stigma.*—Color: Light orange, Orange Group 28D.

The Fruit

Fertility: Low.

Shape: Ovoid.

Color at maturity: Soft Brown.

I claim:

1. A new and distinct cultivar of Longiflorum-Asiatic hybrid lily plant substantially as herein shown and described.

* * * * *